(12) United States Patent
Metges et al.

(10) Patent No.: US 11,391,710 B2
(45) Date of Patent: Jul. 19, 2022

(54) PREDICTION METHOD FOR METHANE ($CH_4$) EMISSION OF A DAIRY COW (71) Applicant: Leibniz-Institut für Nutztierbiologie, Dummerstorf (DE)

(72) Inventors: Cornelia C. Metges, Berlin (DE); Stefanie W. Engelke, Rostock (DE); Gürbüz Das, Rostock (DE); Björn Kuhla, Dummerstorf (DE)

(73) Assignee: Leibniz-Institut für Nutztierbiologie, Dummerstorf (DE)

( * ) Notice: Subject to any disclaimer, the term of this patent is extended or adjusted under 35 U.S.C. 154(b) by 381 days.

(21) Appl. No.: 16/643,008

(22) PCT Filed: Aug. 30, 2018

(86) PCT No.: PCT/EP2018/073327
§ 371 (c)(1),
(2) Date: Feb. 28, 2020

(87) PCT Pub. No.: WO2019/043091
PCT Pub. Date: Mar. 7, 2019

(65) Prior Publication Data
US 2020/0309758 A1 Oct. 1, 2020

(30) Foreign Application Priority Data
Sep. 1, 2017 (EP) .................... 17189083

(51) Int. Cl.
G01N 33/06 (2006.01)
G01N 21/3577 (2014.01)
A23K 50/10 (2016.01)

(52) U.S. Cl.
CPC ............. *G01N 33/06* (2013.01); *A23K 50/10* (2016.05); *G01N 21/3577* (2013.01)

(58) Field of Classification Search
CPC ..... G01N 33/06; G01N 21/3577; A23K 50/10
See application file for complete search history.

(56) References Cited

U.S. PATENT DOCUMENTS 7,966,971 B2 * 6/2011 Zimmerman ........ A01K 29/005
119/51.02
8,307,785 B2 * 11/2012 Zimmerman .......... A61B 5/097
119/51.02

(Continued)

OTHER PUBLICATIONS

Benchaar et al. (2015) Linseed oil supplementation to dairy cows fed diets based on red clover silage or corn silage: Effects on methane production, rumen fermentation, nutrient digestibility, N balance, and milk production. J Dairy Sci 98 (11):7993-8008. doi:10.3168/jds.2015-9398.

(Continued)

*Primary Examiner* — Rebecca C Bryant
(74) *Attorney, Agent, or Firm* — Armstrong Teasdale LLP (57) ABSTRACT

Described herein is a method for predicting the methane ($CH_4$) emission of a dairy cow, the method including:
a) determining the total amount of milk of a dairy cow per one day;
b) determining the energy corrected milk value (ECM) of the milk of the dairy cow of the same day);
c) determining the percentage amount of saturated fatty acids (SFAs) of the total milk fat of the dairy cow of the same day) and the percentage amount of stearic acid (C18:0) of the total milk fat of the dairy cow of the same day;
d) calculating the daily amount of methane emitted by the dairy cow based on the ECM as determined according to b), the percentage amount of SFAs of the total milk fat as determined according to c), and the percentage amount of C18:0 of the total milk fat as determined according to c).

6 Claims, 1 Drawing Sheet

(56) References Cited

U.S. PATENT DOCUMENTS

| | | | |
|---|---|---|---|
| 8,453,601 B2* | 6/2013 | Zimmerman | A61P 37/04 |
| | | | 119/51.02 |
| 9,035,250 B2* | 5/2015 | Weill | G01N 33/04 |
| | | | 702/19 |
| 9,164,081 B2* | 10/2015 | Van Der Tol | A01K 29/005 |
| 2013/0218477 A1 | 8/2013 | Weill et al. | |

OTHER PUBLICATIONS

Castro-Montoya et al. (2016) Predictions of methane emission levels and categories based on milk fatty acid profiles from dairy cows. Animal:1-10. doi:10.1017/s1751731116002627.

Chilliard et al. (2009) Milk fatty acids in dairy cows fed whole crude linseed, extruded linseed, or linseed oil, and their relationship with methane output. J Dairy Sci 92 (10):5199-5211. doi:10.3168/jds.2009-2375.

De Marchi et al. (2014) Invited review: Mid-infrared spectroscopy as phenotyping tool for milk traits. J Dairy Sci 97 (3):1171-1186. doi:10.3168/jds.2013-6799.

Dehareng et al. (2012) Potential use of milk mid-infrared spectra to predict individual methane emission of dairy cows. Animal 6 (10):1694-1701. doi:10.1017/S1751731112000456.

Derno et al. (2009) Technical note: A new facility for continuous respiration measurements in lactating cows. J Dairy Sci 92 (6):2804-2808. doi:10.3168/jds.2008-1839.

Dijkstra et al. (2011) Relationships between methane production and milk fatty acid profiles in dairy cattle. Anim Feed Sci Tech 166-167:590-595. doi:10.1016/j.anifeedsci.2011.04.042.

Ferlay et al. (2013) Effects of incremental amounts of extruded linseed on the milk fatty acid composition of dairy cows receiving hay or corn silage. J Dairy Sci 96 (10):6577-6595. doi:10.3168/jds.2013-6562.

GfE (Gesellschaft für Ernährungsphysiologie) (2001) Empfehlungen zur Energie- und Nährstoffversorgung der Milchkühe und Aufzuchtrinder (Recommended energy and nutrient supply for dairy cows and growing cattle). DLG-Verlag, Frankfurt am Main, Germany. 132 pages. Cited in specification, English translation unavailable.

Glasser et al. (2008) Oilseed lipid supplements and fatty acid composition of cow milk: A meta-analysis. J Dairy Sci 91 (12):4687-4703. doi:10.3168/jds.2008-0987.

Hill et al. (2016) Measuring Methane Production from Ruminants. Trends Biotechnol 34 (1):26-35. doi:10.1016/j.tibtech.2015.10.004.

Hristov et al. (2013) Mitigation of greenhouse gas emissions in livestock production: A review of technical options for non-CO2 emissions. Food and Agriculture Organization of the United Nations (FAO), Rome, Italy, 22 pages.

Kandel et al. (2015) Assessing variability of literature based methane indicator traits in a large dairy cow population. Biotechnol Agron Soc 19 (1):11-19.

Kliem et al. (2008) Effect of replacing grass silage with maize silage in the diet on bovine milk fatty acid composition. Animal 2 (12):1850-1858. doi:10.1017/s1751731108003078.

Knapp Jr, et al. (2014) Invited review: Enteric methane in dairy cattle production: Quantifying the opportunities and impact of reducing emissions. JDairy Sci 97 (6):3231-3261. doi:10.3168/jds.2013-7234.

Maia et al. (2007) Metabolism of polyunsaturated fatty acids and their toxicity to the microflora of the rumen. Anton Leeuw Int J G 91 (4):303-314. doi:10.1007/s10482-006-9118-2.

Martin et al. (2016) Increasing linseed supply in dairy cow diets based on hay or corn silage: Effect on enteric methane emission, rumen microbial fermentation, and digestion. J Dairy Sci 99 (5):3445-3456. doi:10.3168/ids.2015-10110.

Martin et al. (2008) Methane output and diet digestibility in response to feeding dairy cows crude linseed, extruded linseed, or linseed oil. J Anim Sci 86 (10):2642-2650. doi:10.2527/jas.2007-0774.

Meignan et al. (2017) Effects of feeding extruded linseed on production performance and milk fatty acid profile in dairy cows: A meta-analysis. J Dairy Sci. doi:10.3168/jds.2016-11850. 15 pages.

Moate P J et al: "Wheat is more potent than corn or barley for dietary mitigation of enteric methane emissions from dairy cows." Journal of Dairy Science, vol. 100, No. 9, Jul. 12, 2017 (Jul. 12, 2017) pp. 7139-7153.

Mohammad et al. (2011) Prediction of enteric methane output from milk fatty acid concentrations and rumen fermentation parameters in dairy cows fed sunflower, flax, or canola seeds. J Dairy Sci 94 (12):6057-6068. doi:10.3168/jds.2011-4369.

Pickering et al. (2015) Animal board invited review: genetic possibilities to reduce enteric methane emissions from ruminants. Animal 9 (9):1431-1440. doi:10.1017/s1751731115000968.

Rico et al. (2016) Prediction of enteric methane emissions from Holstein dairy cows fed various forage sources. Animal 10 (2):203-211. doi:10.1017/s1751731115001949.

Soyeurt et al. (2011) Mid-infrared prediction of bovine milk fatty acids across multiple breeds, production systems, and countries. J Dairy Sci 94 (4):1657-1667. doi:10.3168/jds.2010-3408.

Spiekers et al. (2004): Erfolgreiche Milchviehfütterung. 4. edition, DLG-Verlag, Frankfurt. 7 pages provided of book cited in specification. English translation unavailble.

Van Gastelen et al. (2015) Enteric methane production, rumen volatile fatty acid concentrations, and milk fatty acid composition in lactating Holstein-Friesian cows fed grass silage- or corn silage-based diets. J Dairy Sci 98 (3):1915-1927. doi:10.3168/jds.2014-8552.

Van Gastelen et al. (2016) Prediction of methane emission from lactating dairy cows using milk fatty acids and mid-infrared spectroscopy. J Sci Food Agric 96 (12):3963-3968. doi:10.1002/jsfa.7718.

Van Lingen et al. (2014) Meta-analysis of relationships between enteric methane yield and milk fatty acid profile in dairy cattle. J Dairy Sci 97 (11):7115-7132. doi:10.3168/jds.2014-8268.

Vanlierde et al. (2015) Hot topic: Innovative lactation-stage-dependent prediction of methane emissions from milk mid-infrared spectra. J Dairy Sci 98 (8):5740-5747. doi:10.3168/jds.2014-8436.

Vanrobays et al. (2016) Changes throughout lactation in phenotypic and genetic correlations between methane emissions and milk fatty acid contents predicted from milk mid-infrared spectra. J Dairy Sci 99 (9):7247-7260. doi:10.3168/jds.2015-10646.

International Search Report and Written Opinion for International Patent Application No. PCT/EP2018/073327, dated Nov. 30, 2018, 11 pages.

\* cited by examiner

Fig. 1

PREDICTION METHOD FOR METHANE (CH$_4$) EMISSION OF A DAIRY COW

CROSS-REFERENCE TO RELATED APPLICATIONS

This application is a U.S. National Phase Application of International Patent Application No. PCT/EP2018/073327, filed Aug. 30, 2018, which claims the benefit of priority to European Patent Application No. 17189083.3, filed Sep. 1, 2017, the entire contents of which are hereby incorporated by reference herein.

FIELD OF THE INVENTION

The present invention relates to a method for predicting the methane (CH$_4$) emission of a dairy cow comprising: determining the total amount of milk of a dairy cow per one day (a); determining the energy corrected milk value (ECM) of the milk of the dairy cow of the same day as in a) (b); determining the percentage amount of saturated fatty acids (SFAs) of the total milk fat of the dairy cow of the same day as in a) and the percentage amount of stearic acid (C18:0) of the total milk fat of the dairy cow of the same day as in a) (c); and calculating the daily amount of methane emitted by the dairy cow based on the ECM as determined according to (b), the percentage amount of SFAs of the total milk fat as determined according to (c) and the percentage amount of C18:0 of the total milk fat as determined according to (c).

BACKGROUND

Livestock contributes about 18% to global anthropogenic greenhouse gas emission (Hristov et al. 2013), wherein cattle represent a main portion of livestock. Methane mitigation opportunities by feeding and genetic selection have been reported to range from 2.5 to 19% in cattle (Knapp et al. 2014; Pickering et al. 2015). Although breeding low-methane emitting cows seems to be possible through genetic selection, this requires determination of methane emission in large numbers of individuals using respiration chambers or the SF6 method. Large scale measurements in respiration chambers, although the gold standard for methane quantification, are not feasible (Hill et al. 2016) for farm animals. Biochemical relationships between rumen fermentation, CH$_4$ production, and milk fatty acid composition suggest the usefulness of milk fatty acid profiles to predict methane emission (liter/day) (Knapp et al. 2014; van Lingen et al. 2014). There are several reports on the relationship between milk fatty acids and methane emission as well as on equations predicting methane yield defined as liter of CH$_4$ per kg dry matter intake and methane intensity defined as liter of CH$_4$ per kg energy corrected milk (Castro-Montoya et al. 2016; Dijkstra et al. 2011; van Lingen et al. 2014).

Quantification of fatty acids is usually done by gas chromatography, the standard procedure to measure the concentration of a large number of fatty acids with high accuracy and precision. However, gas chromatography is unsuitable for routine milk fatty acids determination, but infrared spectroscopy reliably predicted major milk fatty acids and groups of fatty acids (De Marchi et al. 2014; Soyeurt et al. 2011). Infrared spectra from milk are inexpensively recordable on a large scale but have only a moderate power for predicting minor single milk fatty acids (Van Gastelen and Dijkstra 2016; De Marchi et al., 2014).

Although earlier studies reported prediction models based on global infrared milk spectra (Dehareng et al. 2012; Vanlierde et al. 2015), there is so far no published methane prediction equation based on fatty acid composition derived from infrared spectroscopy.

Dry matter intake is the main determinant for CH$_4$ emission (Hristov et al. 2013; Knapp et al. 2014), but cow-individual feed intake information is not available on farms. The object of the present invention was therefore the provision of a method for predicting the methane emission of a dairy cow which does not require knowledge of the daily dry matter intake. The method should be usable for dairy cows, of which feed intake on an individual basis is not known.

SUMMARY

According to the present invention, it was found that this object can be solved by a method for predicting the methane (CH$_4$) emission of a dairy cow comprising:
a) determining the total amount of milk (M) of a dairy cow per one day;
b) determining the energy corrected milk value (ECM) of the milk of the dairy cow of the same day as in a);
c) determining the percentage amount of saturated fatty acids (SFAs) of the total milk fat of the dairy cow of the same day as in a) and the percentage amount of stearic acid (C18:0) of the total milk fat of the dairy cow of the same day as in a);
d) calculating the daily amount of methane emitted by the dairy cow based on the ECM as determined according to (b), the percentage amount of SFAs of the total milk fat as determined according to (c) and the percentage amount of C18:0 of the total milk fat as determined according to (c).

DETAILED DESCRIPTION

In a preferred embodiment, the calculation of the daily amount of methane emitted by the dairy cow according to (d) is based on regression equation 1:

$$\text{CH}_4 \text{ [liter/day]} = -1363.7 + 9.58 \times \text{ECM [kg/day]} + 18.5 \times \text{SFAs [\%]} + 32.4 \times \text{C18:0[\%]} \quad \text{—equation 1—}$$

In contrast to cow-individual intake information, individual records of energy corrected milk, which is highly related to dry matter intake (Hristov et al. 2013), are readily available. It was found that CH$_4$ emission could be predicted from milk fatty acids determined by infrared spectroscopy and that the integration of energy corrected milk improves the prediction power.

The method of the present invention, preferably based on regression equation 1, can be used irrespective of the diet type and applies to ad libitum feeding, meaning that the dairy cow, who's milk is used for the method, has been under an ad libitum feeding regime.

The total amount of milk of a dairy cow per one day (M) is determined by means known in the art. For example, the milk obtained by milking can be collected and the weight thereof can be determined, preferably by measuring the total volume of the milk of the dairy cow per day and calculating, preferably under consideration of the milk's density, its total weight. M is preferably expressed in kg per day. It goes without saying that all determination steps (a), (b) and (c) and also the calculation step (d) are done based on milk or a milk sample respectively, which have been obtained by milking. Since milking is the common central step in milk industry, milk and milk samples respectively are available per se. Thus, the method is typically an ex vivo method carried out on existing milk of a dairy cow and does not require any physical interaction with said dairy cow.

In the context of the present invention the term "percentage" always refers to weight percentage and "%" represents "weight-%". Determining the percentage amount of saturated fatty acids in the total milk fat of the dairy cow of the same day as in a) and the percentage amount of stearic acid of the total milk fat of the dairy cow of the same day as in a) can be done by means and methods known in the art. Preferably, infrared spectroscopy is applied. Determining the percentage amount of saturated fatty acids (SFAs) of the total milk fat of the dairy cow of the same day as in a) and the percentage amount of stearic acid (C18:0) of the total milk fat of the dairy cow of the same day as in a) by infrared spectroscopy means that an infrared spectrum of the milk of the dairy cow is recorded and the respective values such as percentage amount of saturated fatty acids and separately the percentage amount of stearic acid, each based on the total milk fat, are determined from the spectrum by means and methods known to the skilled person. For example, the determination can be done using a MilcoScan milk analysator, for example a MilcoScan FT6000 (Foss, Hilleroed, Denmark), which is based on FTIR technology and works with the mid-Infrared region of the spectrum from 3-10 μm corresponding to 1000-5000 $cm^{-1}$. The percentage amount of saturated fatty acids of the total milk fat according to (c) is at least the sum of the percentage amounts of capric acid (C10:0), myristic acid (C14:0), palmitic acid (C16:0) and stearic acid (C18:0), preferably the sum of at least the percentage amounts of butanoic acid (C4:0), hexanoic acid (C6:0), octanoic acid (C8:0), capric acid (C10:0), lauric acid (C12:0), iso-lauric acid (C12:0-iso), anteiso-lauric acid (C12:0-anteiso), tridecanoic acid (C13:0), myristic acid (C14:0), iso-myristic acid (C14:0-iso), anteiso-myristic acid (C14:0-anteiso), pentadecanoic acid (C15:0), iso-pentadecanoic acid (C15:0-iso), palmitic acid (C16:0), iso-palmitic acid (C16:0-iso), anteiso-palmitic acid (C16:0-anteiso), heptadecanoic acid (C17:0), iso-heptadecanoic acid (C17:0-iso), anteiso-heptadecanoic acid (C17:0-anteiso), stearic acid (C18:0), nonadecanoic acid (C19:0), eicosanoic acid (C20:0) and docosanoic acid (C22:0) of the total milk fat. The percentage amount of stearic acid (C18:0) of the total milk fat, is quantified individually in addition. The expression "total milk fat" means all fat which is detectable in milk as done, for example, in milk testing laboratories. Preferably, the total milk fat is determined by infrared spectroscopy according to DIN ISO 9622 (2017-04), preferably at wave lengths in the range of from 25-2.5 μm. Alternatively, total milk fat can be determined by chemical methods, for example, Röse-Gottlieb- (RG-), Schmidt-Bondzynski-Ratzlaff- (SBR-) or Weibull-Berntrop- (WB-) method.

The energy corrected milk value (ECM) of the milk of the dairy cow of the same day as in a) is also determined by a method known in the art, i.e. the ECM according to (b) is determined according to regression equation 2 (Spiekers et al. 2004):

$$ECM\ [kg/day] = ((1.05 + 0.38 \times F\ [\%] + 0.21 \times P\ [\%])/3.28) \times M\ [kg/day] \quad \text{—equation 2—}$$

wherein:
"M" means the total amount of milk of a dairy cow per one day as determined in (a);
"F" means the percentage amount of total milk fat contained in the milk of the dairy cow per one day as determined in (a); and
"P" means the percentage amount of protein contained in the milk of a dairy cow per one day as determined in (a).

"F" and "P" can be determined by methods known in the art. For example, the percentage amount of total milk fat contained in the milk of the dairy cow per one day can also be determined by infrared spectroscopy. Methods and means for determining the percentage amount of total milk fat contained in the milk of the dairy cow are known in the art. For example, the determination can also be done using a MilcoScan milk analysator, for example a MilcoScan FT6000 (Foss, Hilleroed, Denmark), which is based on Fourier Transform InfraRed (FTIR) analysis. It preferably works with the mid-Infrared region of the spectrum from 3-10 μm corresponding to 1000-5000 $cm^{-1}$. The percentage amount of protein contained in the milk of a dairy cow, can be determined by, for example, by a MilcoScan FT6000 (Foss, Hilleroed, Denmark), which is based on FTIR technology and works with the mid-Infrared region of the spectrum from 3-10 μm corresponding to 1000-5000 $cm^{-1}$.

Below, the work done by the inventors in order to arrive at regression equation 1 is outlined in more detail.

Materials and Methods

1. Animals, Experimental Design and Diets

Ethical approval of the study was obtained (permission no. 7221.3-1-014/14). Twenty half-sib German Holstein cows (106±28 days in milk, 29.5±7.7 kg energy corrected milk per day, 580±57 kg bodyweight, mean±standard deviation) in second (15 cows) or third lactation (5 cows) were used. Cows were kept in tie-stalls, with water and total mixed rations for ad libitum intake. Two isoenergetic total mixed rations, in which the major forage component was either corn silage or grass silage, supplemented with or without linseed were used (7 MJ $NEL$/kg dry matter; Table 1).

TABLE 1

Ingredients and chemical composition of experimental total mixed ration consisting of basal rations based on grass silage or corn silage with and without linseed supplementation (means ± standard deviation; n = 5). Dry matter, fresh matter, ash-free neutral detergent fiber, acid detergent fiber, and net energy for lactation are abbreviated as DM, FM, aNDF, ADF and $NE_L$. The linseed product (Omegalin 60; Spezialfutter Neuruppin GmbH und Co. KG, Neuruppin, Germany) contained 60% of extruded linseed (Tradilin ®) and 40% of wheat bran with 25% crude fat including 6% palmitic acid (C16:0), 18.4% oleic acid (C18:1cis9), 18.5% linoleic acid (C18:2cis9, cis12) and 55% linolenic acid (C18:3cis9, cis12, cis15). Concentrate (MF 2000; Vollkraft Mischfutterwerke GmbH, Güstrow, Germany) consisted of 33% extracted soy meal, 20% corn, 17% wheat gluten, 8% extracted rapeseed meal, 5% sugar beet pulp, 2% sodium hydrogen carbonate, 1.3% calcium carbonate, 0.2% sodium chloride; "—" not added.

| Ingredient | Grass silage | | Corn silage | |
|---|---|---|---|---|
| (g/kg DM) | No linseed | Linseed | No linseed | Linseed |
| Grass silage | 343 ± 31.0 | 380 ± 15.0 | 122 ± 21.5 | 142 ± 34.3 |
| Corn silage | 181 ± 33.2 | 195 ± 37.9 | 445 ± 46.7 | 452 ± 44.0 |

TABLE 1-continued

Ingredients and chemical composition of experimental total mixed ration consisting of basal rations based on grass silage or corn silage with and without linseed supplementation (means ± standard deviation; n = 5). Dry matter, fresh matter, ash-free neutral detergent fiber, acid detergent fiber, and net energy for lactation are abbreviated as DM, FM, aNDF, ADF and $NE_L$. The linseed product (Omegalin 60; Spezialfutter Neuruppin GmbH und Co. KG, Neuruppin, Germany) contained 60% of extruded linseed (Tradilin ®) and 40% of wheat bran with 25% crude fat including 6% palmitic acid (C16:0), 18.4% oleic acid (C18:1cis9), 18.5% linoleic acid (C18:2cis9, cis12) and 55% linolenic acid (C18:3cis9, cis12, cis15). Concentrate (MF 2000; Vollkraft Mischfutterwerke GmbH, Güstrow, Germany) consisted of 33% extracted soy meal, 20% corn, 17% wheat gluten, 8% extracted rapeseed meal, 5% sugar beet pulp, 2% sodium hydrogen carbonate, 1.3% calcium carbonate, 0.2% sodium chloride; "—" not added.

| Ingredient | Grass silage | | Corn silage | |
|---|---|---|---|---|
| (g/kg DM) | No linseed | Linseed | No linseed | Linseed |
| Straw, barley | 52 ± 7.0 | 61 ± 23.2 | 40 ± 7.2 | 34 ± 10.3 |
| Grass hay | 81 ± 12.0 | 94 ± 22.0 | 43 ± 3.1 | 44 ± 3.0 |
| Corn, ground | — | — | 93 ± 9.2 | 25 ± 27.2 |
| Soy extract meal | 25 ± 26.8 | 40 ± 19.2 | 114 ± 14.2 | 87 ± 9.2 |
| Barley, ground | 100 ± 17.9 | — | — | — |
| Wheat, ground | 101 ± 9.8 | — | — | — |
| Linseed product | — | 143 ± 11.4 | — | 137 ± 9.9 |
| Concentrate | 109 ± 20 | 79 ± 13.0 | 129 ± 7.3 | 65 ± 32.6 |
| Mineral/vitamin mix | 9 ± 0.5 | 10 ± 0.6 | 10 ± 0.6 | 10 ± 0.6 |
| Calcium carbonate | — | — | 4.1 ± 0.3 | 4 ± 0.3 |
| DM (g/kg of FM) | 468 ± 33.0 | 452 ± 450 | 446 ± 32.0 | 439 ± 33.0 |
| Nutrients (g/kg of DM) | | | | |
| Crude ash | 69.9 ± 2.8 | 75.8 ± 2.5 | 66.1 ± 3.0 | 65.7 ± 4.2 |
| Crude protein | 161 ± 9.0 | 173 ± 14.4 | 169 ± 11.7 | 163 ± 11.1 |
| Crude fiber | 166 ± 7.9 | 186 ± 7.1 | 155 ± 3.3 | 161 ± 4.5 |
| Crude fat | 28.1 ± 1.7 | 58.3 ± 7.8 | 29.8 ± 2.4 | 56.4 ± 6.5 |
| Sugar | 51.3 ± 15.7 | 50.1 ± 16.2 | 31.4 ± 7.9 | 30.3 ± 11.1 |
| Starch | 218 ± 12.0 | 110 ± 18.7 | 261 ± 25.4 | 216 ± 34.5 |
| aNDF | 371 ± 18.1 | 410 ± 12.9 | 330 ± 10.9 | 352 ± 9.2 |
| ADF | 198 ± 9.8 | 224 ± 7.9 | 186 ± 5.4 | 194 ± 5.0 |
| $NE_L$ (MJ/kg of DM) | 6.9 ± 0.2 | 6.9 ± 0.1 | 7.0 ± 0.1 | 7.1 ± 0.1 |

Randomly selected 10 cows were fed on corn silage based diets for 5 weeks without and for another 5 weeks with linseed supplementation in randomized order (Periods A and B: experimental weeks 1 to 5, and 7 to 11, respectively; step-wise change of rations in experimental weeks 0 and 6). The other 10 cows were allocated randomly to grass silage diets without or with linseed supplementation for 5 weeks each. The study was conducted in 5 experimental runs each with 4 cows. All four diets were fed simultaneously in each run. Cows were fed twice daily at 0730 and 1730 hours; dry matter intake was recorded daily. Three cows feeding on the grass silage based diet supplemented with linseed had to be removed because of illness or feed refusal. The nutrient contents of the diets were in line with recommendations of the German Society of Nutritional Physiology (GfE 2001).

2. Determination of Feed and Milk Composition and Methane Production

Analyses of feed nutrient composition (Table 1) were performed by a certified feed laboratory. During the respiration measurements aliquots of one evening and morning milking were pooled. Milk fat and fatty acid composition was analysed using infrared spectroscopy (MilcoScan FT6000; Foss, Hilleroed, Denmark) by a commercial laboratory (Comité du Lait, Battice, Belgium). Saturated and unsaturated fatty acids, as well as isomers of C18:1cis and trans and ω-3 fatty acids were quantified as groups (Table 2).

TABLE 2

Composition of groups of milk fatty acids analyzed using infrared spectroscopy.

| Group | Fatty acids |
|---|---|
| Saturated fatty acids | C4:0 |
| | C6:0 |
| | C8:0 |
| | C10:0 |
| | C12:0 |
| | C12:0-iso |
| | C12:0-anteiso |
| | C13:0-iso |
| | C14:0 |
| | C14:0-iso |
| | C14:0-anteiso |
| | C14:0 |
| | C15:0 |
| | C15:0-iso |
| | C16:0 |
| | C16:0-iso |
| | C16:0-anteiso |
| | C17:0 |
| | C17:0-iso |
| | C17:0-anteiso |
| | C18:0 |
| | C19:0 |
| | C20:0 |
| | C22:0 |
| Unsaturated fatty acids | C10:1 |
| | C12:1cis of summed isomers |
| | C14:1cis of summed isomers |
| | C16:1cis of summed isomers |
| | C16:1trans of summed isomers |
| | C18:1cis9 |
| | C18:1cis11 |
| | C18:1cis12 |
| | C18:1trans6 + 7 + 8 + 9 + 10 + 11 isomers |
| | C18:1trans12 + 13 + 14 isomers |
| | C18:1cis13 + cis14 + trans16 isomers |
| | C20:1cis9 |
| | C20:1cis11 |
| | C18:2cis9, trans11 |
| | C18:3cis9, cis12, cis15 |
| | C20:3 ω-6 |
| | C20:4 ω-6 |
| | C20:5 ω-3 |
| | C22:5 ω-3 |
| Monounsaturated fatty acids | % of unsaturated fatty acids |
| Polyunsaturated fatty acids | % of unsaturated fatty acids |
| C18:1cis | Total sum of isomers |
| C18:1trans | Total sum of isomers (6 to 14) |
| Omega-3 fatty acids | C18:3cis9, cis12, cis15 |
| | C20:5 ω-3 |
| | C22:5 ω-3 |

Mono- and polyunsaturated fatty acids were expressed as percentage of unsaturated fatty acids in total milk fat. Palmitic acid (C16:0) and stearic acid (C18:0) were quantified individually each as percentage in total milk fat.

Individual methane emission was quantified in experimental weeks 5 and 11 for two subsequent 24-hours periods (0700 to 0700 hours; i.e. from 07.00 to 07.00 hours next day) using respiration chambers, after cows have been placed in the chambers for >15 h with their respective rations (Demo et al. 2009). The $CH_4$ recovery in the chambers was 99.8%. In the chambers temperature and relative humidity were 15° C. and 60%, respectively, and light was on from 0600 to 1900 hours. Feed intake was recorded continuously and summarized over 24 hours. Residual feed was removed from the trough before cows were offered fresh feed at 0730 and 1730 hours. Cows were milked at 0630 and 1630 hours.

3. Calculations and Statistical Analyses 3.1 Analysis of Variance

Data were analysed using SAS (SAS/STAT 9.3; SAS Institute Inc. 2011, Cary, N.C.). The dependent variables $CH_4$ emission, dry matter intake and energy corrected milk averaged per 24 hours were analyzed with repeated measures analysis of variance using PROC MIXED. The model contained the fixed effects of basal ration (corn silage or grass silage based), linseed supplementation (with and without), the interaction effect between basal ration and linseed supplementation as well as effects of experimental runs (1-5), periods (A or B) and the order (linseed in period A or B first). The covariance structure was Compound Symmetry. Effects were considered significant at $P \leq 0.05$. There were no interaction effects between basal ration and linseed supplementation and data are presented for basal ration and linseed supplementation categories (Table 3).

TABLE 3

Dry matter intake (DMI), energy corrected milk (ECM), methane emission($CH_4$) per day, per energy corrected milk ($CH_4$/ECM) and per dry matter intake ($CH_4$/DMI) and milk fatty acid composition of lactating cows housed in respiration chambers receiving rations based on grass silage (GS) or corn silage (CS) with (LS) and without (L0) linseed supplementation. Unsaturated fatty acids are abbreviated as UFA. There was no significant interaction between basal ration and linseed supplementation (P > 0.14).

|  | Basal ration | | | | Linseed supplementation | | | |
| --- | --- | --- | --- | --- | --- | --- | --- | --- |
|  | GS | CS | SE | P, ≤ | L0 | LS | SE | P, ≤ |
| DMI (kg/day) | 15.4 | 18.3 | 0.83 | 0.024 | 17.4 | 16.3 | 0.66 | 0.061 |
| ECM (kg/day) | 22.3 | 28.7 | 1.19 | 0.002 | 25.8 | 25.2 | 0.92 | 0.334 |
| Milk fat (g/l) | 46.0 | 40.5 | 1.67 | 0.032 | 44.1 | 42.4 | 1.36 | 0.206 |
| Methane production | | | | | | | | |
| $CH_4$ (l/day) | 480 | 544 | 25.11 | 0.089 | 547 | 477 | 20.24 | 0.002 |
| $CH_4$/ECM (l/kg) | 22.3 | 19.0 | 1.08 | 0.050 | 21.7 | 19.5 | 0.85 | 0.006 |
| $CH_4$/DMI (l/kg) | 32.3 | 29.6 | 1.73 | 0.289 | 31.9 | 30.0 | 1.27 | 0.011 |
| Fatty acid (% of total milk fat) | | | | | | | | |
| Saturated | 65.7 | 66.3 | 1.07 | 0.684 | 72.1 | 59.8 | 0.84 | 0.001 |
| Unsaturated | 34.4 | 33.7 | 1.07 | 0.684 | 27.9 | 40.2 | 0.84 | 0.001 |
| Mono- (% UFA) | 87.2 | 86.6 | 0.23 | 0.060 | 87.2 | 86.7 | 0.20 | 0.053 |
| Poly- (% UFA) | 12.8 | 13.4 | 0.23 | 0.060 | 12.8 | 13.4 | 0.20 | 0.053 |
| C16:0 | 27.8 | 27.8 | 0.89 | 0.988 | 32.2 | 23.3 | 0.75 | 0.001 |
| C18:0 | 12.6 | 12.8 | 0.27 | 0.500 | 10.5 | 15.0 | 0.24 | 0.001 |
| C18:1cis | 22.9 | 22.5 | 0.76 | 0.735 | 18.7 | 26.7 | 0.60 | 0.001 |
| C18:1trans | 3.83 | 3.90 | 0.18 | 0.788 | 2.58 | 5.15 | 0.15 | 0.001 |
| ω-3 | 0.80 | 0.82 | 0.02 | 0.556 | 0.70 | 0.92 | 0.02 | 0.001 |

3.2 Regression and Correlations

Methane emission and $CH_4$ intensity were estimated using multiple linear regression models with the stepwise explanatory-independent variable selection method for each diet separately. Similarly, methane emission was also estimated by using combined data categorized by basal diets or linseed supplementation, as well as for all available data across 4 diets. For the regression analysis, two data sets with different independent explanatory variables were made available. Explanatory variables of the stepwise variable selection were considered if $P \leq 0.15$. The first data set included milk fatty acid concentrations only, whereas the second one additionally included energy corrected milk yield. Agreement between predicted and measured methane emissions was assessed by correlation analysis.

Results and Discussion

1. Feed Intake, Performance, and Methane Emission

Cows fed the corn silage based diets tended to show a greater $CH_4$ emission as compared to cows fed the grass silage based diets (P=0.089; Table 3). In contrast, $CH_4$ yield was similar among basal diets, and $CH_4$ intensity was lower (P=0.050) by about 15% with corn as compared to grass silage based rations. Methane yield of dairy cows fed grass silage and corn silage based diets and/or fat additives reported by others (Benchaar et al. 2015; Martin et al. 2016; Mohammed et al. 2011) were comparable to the present results. The lowering of $CH_4$ intensity in corn silage based diets was mainly due to higher levels of energy corrected milk (Table 3) irrespective of dry matter intake. Starch fermentation in the rumen favors the production of propionate which occurs at higher levels when corn silage instead of grass silage based diets are fed (Knapp et al. 2014; van Gastelen et al. 2015). This is linked to a decreased rumen pH and a lower production of $H_2$ which reduces the activity of methanogens (Knapp et al. 2014; van Gastelen et al. 2015). Van Gastelen et al. (2015) observed a reduction in $CH_4$ yield of 11% when corn silage compared to grass silage was fed. Linseed supplementation decreased (P<0.01) $CH_4$ yield by 6%, $CH_4$ intensity by 10% and $CH_4$ emission by 13%. The methane lowering potential of lipids from linseed is a result of the inhibitory effect on fibrolytic bacteria, a lower number of protozoa and the biohydrogenation of unsaturated fatty acids in the rumen (Maia et al. 2007; Martin et al. 2016). A 10% supplementation of extruded linseed reduced $CH_4$ yield by 15% in hay based and 8% in corn silage based diets (Martin et al. 2016). Benchaar et al. (2015) examined a 4% linseed oil supplementation to a corn silage diet and a red clover diet, respectively, and observed 20 and 8% reduction of $CH_4$ yield, respectively. Related to dry matter intake, differences in methane lowering potential in the various studies could be a result of the amount (Martin et al. 2016) and form of linseed supplementation (Martin et al. 2008).

2. Milk Fatty Acid Composition

A greater total milk fat level was observed with grass silage compared to corn silage based diets (P=0.032). Milk fatty acid groups and individual fatty acids concentrations were unaffected by basal rations with the exception of mono and polyunsaturated fatty acids which tended to be lower and higher with corn silage based rations, respectively (P=0.060; Table 3). Dietary fat determines the concentrations of long chain saturated and unsaturated fatty acids in milk fat (Chilliard et al. 2009; Meignan et al. 2017). Grass and corn silage are rich in C18:3 ω-3 and C18:2 ω-6, respectively, explaining their concentrations and that of their bio-hydrogenation products in milk (van Gastelen et al. 2015). Similar to the present results, replacing grass silage with corn silage did not alter total saturated, mono- and polyunsaturated fatty acids, as well as C18:1cis including cis9 concentrations, but proportions of C6:0 to C14:0 and C18:1trans increased while ω-3 fatty acids decreased. Inconsistent results were reported for C18:0 and C16:0 levels that were similar, increased or decreased (Kliem et al. 2008; van Gastelen et al. 2015). This ambiguity is probably due to different dietary levels of grass silage and corn silage, differences in bio-hydrogenation, and possibly differences in de novo synthesis in the mammary gland (Kliem et al. 2008; van Gastelen et al. 2015). We found, that the higher availability of unsaturated fatty acids in linseed supplemented diets lead to higher concentrations of C18:0, ω-3 milk fatty acids, sums of C18:1cis and trans, and groups of unsaturated fatty acids whereas C16:0 and groups of saturated fatty acid levels were lower (P<0.001; Table 3). Linseed tended to decrease the proportion of monounsaturated fatty acids (P=0.053) whilst increasing the corresponding proportion of polyunsaturated fatty acids (P<0.001). It has been shown that 87% of the C18:3 ω-3 intake was bio-hydrogenated (Meignan et al. 2017). Thus diets containing high amounts of C18:3 ω-3 such as linseed diets lead to higher proportions of bio-hydrogenation intermediates like C18:1trans isomers and their end-product C18:0, which can be converted to oleic acid, as well as unsaturated fatty acids which can be found in milk. In contrast, the observed decrease of saturated fatty acids including C16:0 (P<0.001) may be a result of less organic matter and fiber digestibility in the presence of a higher proportion of polyunsaturated fatty acids in the rumen (Maia et al. 2007; Martin et al. 2016). In addition, fatty acid synthesis is inhibited by long chain fatty acid bio-hydrogenation products (Glasser et al. 2008; van Lingen et al. 2014). Others reported comparable changes in saturated and unsaturated fatty acid, C16:0, C18:0, 18:1cis and trans isomers and ω-3 fatty acids levels in their studies, when extruded linseed was supplemented (Chilliard et al. 2009; Ferlay et al. 2013). Mohammed et al. (2011) observed no difference in C18:1trans milk fatty acid concentrations between a 9.3% linseed supplemented diet and a control diet that included 4% Ca salts of palm oil. Notably, in all studies cited gas chromatography was used to determine milk fatty acid concentrations. Although infrared spectroscopy is considered less specific than gas chromatography and the accuracy of quantification of major fatty acids is better than for minor fatty acids (De Marchi et al. 2014) the present results are largely in line with the literature. High accuracies have been shown for infrared predictions of saturated fatty acids, C18:1trans, C18:1cis9, C18:1cis, groups of saturated, unsaturated and monounsaturated fatty acids, and also for the group of ω-3 fatty acids (De Marchi et al. 2014; Soyeurt et al. 2011).

3. Predicting Methane Emission

Many studies reporting prediction equations are based on milk fatty acid concentrations analysed by gas chromatography (Castro-Montoya et al. 2016; Rico et al. 2016; van Lingen et al. 2014). To date published prediction models based on global infrared milk spectra (Kandel et al. 2015; Vanlierde et al. 2015) used the model of Dehareng et al. (2012). Dehareng et al. (2012) included methane production data of 11 cows measured by the SF6 method, and reported a predictive power between 0.68 and 0.79 for g of $CH_4$ per day, and g of $CH_4$ per kg of milk. In the present study two datasets were used to develop multiple regression equations. The data set 1 comprised nine groups of fatty acids or individual fatty acids measured by infrared spectroscopy, the second data set included additionally energy corrected milk yield (Table 4).

TABLE 4

Summary of multiple regression equations predicting methane emission. Each line summarizes a regression equation specific to a single or grouped diets based on combinations of basal ration or linseed supplementation. Data set 1 included milk fatty acids, whereas data set 2 additionally included energy corrected milk (ECM) as independent variable. Equations were developed separately for experimental diets containing grass silage without or with linseed supplementation (GS-L0, GS-LS) and corn silage without or with linseed supplementation (CS-L0, CS-LS) as well as for basal rations (GS, CS), linseed supplementation (L0, LS) and all experimental diets collectively; P* value of the model; "—" not determined.

| $CH_4$ (l/day) | N | Intercept | ECM | SFA | UFA | MUFA | PUFA | C16:0 | C18:0 | C18:1 cis | C18:1 trans | ω-3 fatty acids | $R^2$ | P*≤ |
|---|---|---|---|---|---|---|---|---|---|---|---|---|---|---|
| Data set 1 | | | | | | | | | | | | | | |
| GS-L0 | 9 | −979.3 | Left out | — | — | — | — | 46.18 | — | — | — | — | 0.94 | 0.001 |
| GS-LS | 7 | 1002.2 | Left out | — | — | — | — | — | — | −19.57 | — | — | 0.70 | 0.019 |
| CS-L0 | 10 | −702.6 | Left out | — | — | — | — | 40.36 | — | — | — | — | 0.68 | 0.004 |
| CS-LS | 10 | 1232.7 | Left out | — | — | — | — | — | — | −27.89 | — | — | 0.61 | 0.008 |
| GS | 16 | −2216.7 | Left out | — | — | — | — | 39.67 | 6.88 | 70.81 | — | — | 0.82 | 0.001 |
| CS | 20 | 2350.9 | Left out | — | — | — | — | −24.80 | 71.70 | −50.77 | — | −1093.0 | 0.75 | 0.001 |
| L0 | 19 | −2594.7 | Left out | 22.54 | — | — | — | 27.41 | 61.52 | — | — | — | 0.86 | 0.001 |
| LS | 17 | 1098.9 | Left out | — | — | — | — | — | — | −23.00 | — | — | 0.61 | 0.001 |
| All diets | 36 | −2533.7 | Left out | 33.81 | — | — | — | — | — | 54.97 | 30.91 | — | 0.70 | 0.001 |
| Data set 2 | | | | | | | | | | | | | | |
| GS-L0 | 9 | −979.3 | — | — | — | — | — | 46.18 | — | — | — | — | 0.94 | 0.001 |
| GS-LS | 7 | 1002.2 | — | — | — | — | — | — | — | −19.57 | — | — | 0.70 | 0.019 |
| CS-L0 | 10 | −604.9 | 18.16 | — | — | — | — | 20.81 | — | — | — | — | 0.85 | 0.001 |
| CS-LS | 10 | 27.42 | 16.73 | — | — | — | — | — | — | — | — | — | 0.66 | 0.004 |
| GS | 16 | −1019.9 | 10.64 | — | — | — | — | 27.77 | 38.82 | — | — | — | 0.82 | 0.001 |

TABLE 4-continued

Summary of multiple regression equations predicting methane emission. Each line summarizes a regression equation specific to a single or grouped diets based on combinations of basal ration or linseed supplementation. Data set 1 included milk fatty acids, whereas data set 2 additionally included energy corrected milk (ECM) as independent variable. Equations were developed separately for experimental diets containing grass silage without or with linseed supplementation (GS-L0, GS-LS) and corn silage without or with linseed supplementation (CS-L0, CS-LS) as well as for basal rations (GS, CS), linseed supplementation (L0, LS) and all experimental diets collectively; P* value of the model; "—" not determined.

| $CH_4$ (l/day) | N | Intercept | ECM | SFA | UFA | MUFA | PUFA | C16:0 | C18:0 | C18:1 cis | C18:1 trans | ω-3 fatty acids | $R^2$ | P*≤ |
|---|---|---|---|---|---|---|---|---|---|---|---|---|---|---|
| CS | 20 | 284.1 | 16.82 | — | -6.58 | — | — | — | — | — | — | — | 0.76 | 0.001 |
| L0 | 19 | -558.4 | 10.04 | — | — | — | — | 24.31 | 47.88 | — | — | -616.6 | 0.91 | 0.001 |
| LS | 17 | 721.3 | 7.97 | — | — | — | — | — | — | -16.76 | — | — | 0.71 | 0.001 |
| All diets | 36 | -1363.7 | 9.58 | 18.45 | — | — | — | — | 32.36 | — | — | — | 0.79 | 0.001 |

Figure 1:
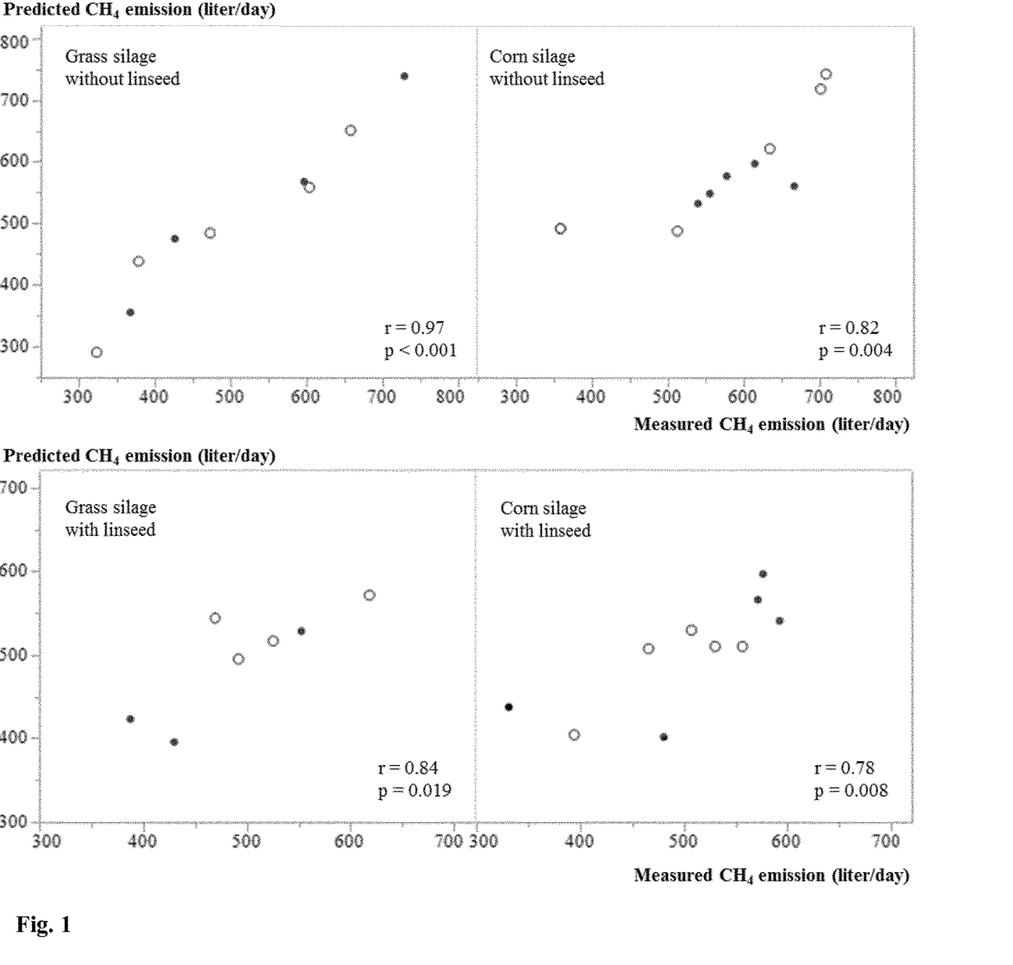
FIG. 1 illustrates measured CH$_4$ emission (x axis) and predicted CH$_4$ emission (y axis) derived from the multiple regression equation for individual experimental diets are shown (grass silage without linseed, corn silage without linseed, grass silage with linseed and corn silage with linseed) considering both periods (filled circle=period A; open circle=period B). The graphical representation highlights the effectiveness of the deduced prediction model. A Pearson correlation coefficient (r) and the probability (p) are given.

Although dry matter intake explains a large part of variation observed in methane emission (Knapp et al. 2014) this information is not available on farms. Thus it cannot be considered as a variable to be implemented in methane prediction equations for on-farm application. This is in contrast to energy corrected milk which is a readily available cow-individual measure reflecting the dry matter intake (Hristov et al. 2013). Consequently, it can be used as a surrogate for dry matter intake. The dry matter intake can explain 52 to 64% of methane emission (Knapp et al. 2014). Using the first data set the goodness of the regression fit for $CH_4$ emission for individual diets ranged from $R^2$=0.61 to 0.94. Measured and predicted methane emission correlated strongly (FIG. 1). Using data of all diets collectively, a coefficient of determination of $R^2$=0.70 was obtained and the corresponding correlation coefficient between measured and predicted methane emission was r=0.84 (P<0.001).

If energy corrected milk was included (data set 2), the goodness of fit was considerably improved relative to the equations of data set 1 in most cases (Table 4). Correlation between measured and predicted methane emission was r=0.89 (P<0.001) for all diets, and ranged from 0.81 to 0.97 (P<0.019) for individual diets.

CONCLUSION

This is the first report on multiple regression equations predicting methane emission based on milk fatty acids analyzed by infrared spectroscopy. The prediction of methane emission using milk fatty acid data of all diets collectively showed moderate to high predictive power. The inclusion of energy corrected milk yield as additional independent variables resulted in improvements of predictive power for all diets collectively by 13%.

CITED LITERATURE

Benchaar C, Hassanat F, Martineau R, Gervais R (2015) Linseed oil supplementation to dairy cows fed diets based on red clover silage or corn silage: Effects on methane production, rumen fermentation, nutrient digestibility, N balance, and milk production. J Dairy Sci 98 (11):7993-8008. doi:10.3168/jds.2015-9398;

Castro-Montoya J M, Peiren N, Veneman J, De Baets B, De Campeneere S, Fievez V (2016) Predictions of methane emission levels and categories based on milk fatty acid profiles from dairy cows. Animal:1-10. doi:10.1017/s1751731116002627;

Chilliard Y, Martin C, Rouel J, Doreau M (2009) Milk fatty acids in dairy cows fed whole crude linseed, extruded linseed, or linseed oil, and their relationship with methane output. J Dairy Sci 92 (10):5199-5211. doi:10.3168/jds.2009-2375;

De Marchi M, Toffanin V, Cassandro M, Penasa M (2014) Invited review: Mid-infrared spectroscopy as phenotyping tool for milk traits1. J Dairy Sci 97 (3):1171-1186. doi:10.3168/jds.2013-6799;

Dehareng F, Delfosse C, Froidmont E, Soyeurt H, Martin C, Gengler N (2012) Potential use of milk mid-infrared spectra to predict individual methane emission of dairy cows. Animal 6 (10):1694-1701. doi:10.1017/51751731112000456;

Derno M, Elsner H G, Paetow E A, Scholze H, Schweigel M (2009) Technical note: A new facility for continuous respiration measurements in lactating cows. J Dairy Sci 92 (6):2804-2808. doi:10.3168/jds.2008-1839

Dijkstra J, van Zijderveld S M, Apajalahti J A, Bannink A, Gerrits W J J, Newbold J R (2011) Relationships between methane production and milk fatty acid profiles in dairy cattle. Anim Feed Sci Tech 166-167:590-595. doi:10.1016/j.anifeedsci.2011.04.042;

Ferlay A, Doreau M, Martin C, Chilliard Y (2013) Effects of incremental amounts of extruded linseed on the milk fatty acid composition of dairy cows receiving hay or corn silage. J Dairy Sci 96 (10):6577-6595. doi:10.3168/jds.2013-6562;

GfE (Gesellschaft für Ernährungsphysiologie) (2001) Empfehlungen zur Energie- und Nährstoffversorgung der Milchkühe und Aufzuchtrinder (Recommended energy and nutrient supply for dairy cows and growing cattle). DLG-Verlag, Frankfurt am Main, Germany;

Glasser F, Ferlay A, Chilliard Y (2008) Oilseed lipid supplements and fatty acid composition of cow milk: A meta-analysis. J Dairy Sci 91 (12):4687-4703. doi:10.3168/jds.2008-0987;

Hill J, McSweeney C, Wright A-DG, Bishop-Hurley G, Kalantar-zadeh K (2016) Measuring Methane Production from Ruminants. Trends Biotechnol 34 (1):26-35. doi:10.1016/j.tibtech.2015.10.004;

Hristov A N, Oh J, Lee C, Meinen R, Montes F, Ott T (eds) (2013) Mitigation of greenhouse gas emissions in livestock production: A review of technical options for non-$CO_2$ emissions. Food and Agriculture Organization of the United Nations (FAO), Rome, Italy;

Kandel P B, Gengler N, Soyeurt H (2015) Assessing variability of literature based methane indicator traits in a large dairy cow population. Biotechnol Agron Soc 19 (1):11-19;

Kliem K E, Morgan R, Humphries D J, Shingfield K J, Givens D I (2008) Effect of replacing grass silage with maize silage in the diet on bovine milk fatty acid composition. Animal 2 (12):1850-1858. doi:10.1017/s1751731108003078;

Knapp J R, Laur G L, Vadas P A, Weiss W P, Tricarico J M (2014) Invited review: Enteric methane in dairy cattle production: Quantifying the opportunities and impact of reducing emissions. J Dairy Sci 97 (6):3231-3261. doi:10.3168/jds.2013-7234;

Maia M R G, Chaudhary L C, Figueres L, Wallace R J (2007) Metabolism of polyunsaturated fatty acids and their toxicity to the microflora of the rumen. Anton Leeuw Int J G 91 (4):303-314. doi:10.1007/s10482-006-9118-2;

Martin C, Ferlay A, Mosoni P, Rochette Y, Chilliard Y, Doreau M (2016) Increasing linseed supply in dairy cow diets based on hay or corn silage: Effect on enteric methane emission, rumen microbial fermentation, and digestion. J Dairy Sci 99 (5):3445-3456. doi:10.3168/jds.2015-10110;

Martin C, Rouel J, Jouany J P, Doreau M, Chilliard Y (2008) Methane output and diet digestibility in response to feeding dairy cows crude linseed, extruded linseed, or linseed oil. J Anim Sci 86 (10):2642-2650. doi:10.2527/jas.2007-0774

Meignan T, Lechartier C, Chesneau G, Bareille N (2017) Effects of feeding extruded linseed on production performance and milk fatty acid profile in dairy cows: A meta-analysis. J Dairy Sci. doi:10.3168/jds.2016-11850;

Mohammed R, McGinn S M, Beauchemin K A (2011) Prediction of enteric methane output from milk fatty acid concentrations and rumen fermentation parameters in dairy cows fed sunflower, flax, or canola seeds. J Dairy Sci 94 (12):6057-6068. doi:10.3168/jds.2011-4369;

Pickering N K, Oddy V H, Basarab J, Cammack K, Hayes B, Hegarty R S (2015) Animal board invited review: genetic possibilities to reduce enteric methane emissions from ruminants. Animal 9 (9):1431-1440. doi:10.1017/s1751731115000968;

Rico D E, Chouinard P Y, Hassanat F, Benchaar C, Gervais R (2016) Prediction of enteric methane emissions from Holstein dairy cows fed various forage sources. Animal 10 (2):203-211. doi:10.1017/s1751731115001949;

Soyeurt H, Dehareng F, Gengler N, McParland S, Wall E, Berry D P (2011) Mid-infrared prediction of bovine milk fatty acids across multiple breeds, production systems, and countries. J Dairy Sci 94 (4):1657-1667. doi:10.3168/jds.2010-3408;

van Gastelen S, Antunes-Fernandes E C, Hettinga K A, Klop G, Alferink S J J, Hendriks W H (2015) Enteric methane production, rumen volatile fatty acid concentrations, and milk fatty acid composition in lactating Holstein-Friesian cows fed grass silage- or corn silage-based diets. J Dairy Sci 98 (3):1915-1927. doi:10.3168/jds.2014-8552;

Spiekers H, Potthast V (2004): Erfolgreiche Milchviehfütterung. 4. edition, DLG-Verlag, Frankfurt;

van Gastelen S, Dijkstra J (2016) Prediction of methane emission from lactating dairy cows using milk fatty acids and mid-infrared spectroscopy. J Sci Food Agric 96 (12):3963-3968. doi:10.1002/jsfa.7718;

van Lingen H J, Crompton L A, Hendriks W H, Reynolds C K, Dijkstra J (2014) Meta-analysis of relationships between enteric methane yield and milk fatty acid profile in dairy cattle. J Dairy Sci 97 (11):7115-7132. doi:10.3168/jds.2014-8268;

Vanlierde A, Vanrobays M L, Dehareng F, Froidmont E, Soyeurt H, McParland S (2015) Hot topic: Innovative lactation-stage-dependent prediction of methane emissions from milk mid-infrared spectra. J Dairy Sci 98 (8):5740-5747. doi:10.3168/jds.2014-8436;

Vanrobays M L, Bastin C, Vandenplas J, Hammami H, Soyeurt H, Vanlierde A (2016) Changes throughout lactation in phenotypic and genetic correlations between methane emissions and milk fatty acid contents predicted from milk mid-infrared spectra. J Dairy Sci 99 (9):7247-7260. doi:10.3168/jds.2015-10646.

The invention claimed is:

1. A method for predicting methane ($CH_4$) emission of a dairy cow, the method comprising:
    a) determining a total amount of milk of a dairy cow per one day;
    b) determining an energy corrected milk value (ECM) of the milk of the dairy cow of the same day as in a);
    c) determining a weight percentage amount of saturated fatty acids (SFAs) of total milk fat of the dairy cow of the same day as in a) and a weight percentage amount of stearic acid (C18:0) of the total milk fat of the dairy cow of the same day as in a);
    d) calculating a daily amount of methane emitted by the dairy cow based on the ECM as determined according to b), the weight percentage amount of SFAs of the total milk fat as determined according to c) and the weight percentage amount of C18:0 of the total milk fat as determined according to c).

2. The method according to claim 1, wherein the calculation of the daily amount of methane emitted by the dairy cow according to d) is based on regression equation 1:

$$CH_4 \text{ [liter/day]}=-1363.7+9.58\times ECM \text{ [kg/day]}+18.5\times SFAs \text{ [\%]}+32.4\times C18:0 \text{ [\%]} \qquad \text{—equation 1—}$$

3. The method according to claim 1, wherein the weight percentage amount of saturated fatty acids (SFAs) of the total milk fat according to c) is at least a sum of weight percentage amounts of capric acid (C10:0), myristic acid (C14:0), palmitic acid (C16:0) and stearic acid (C18:0) of the total milk fat.

4. The method according to claim 1, wherein the weight percentage amount of saturated fatty acids (SFAs) according to c) and the weight percentage amount of stearic acid (C18:0) according to c) of the total milk fat of the dairy cow is determined by infrared spectroscopy.

5. The method according to claim 1, wherein the ECM according to b) is determined according to regression equation 2:

$$ECM \text{ [kg/day]}=((1.05+0.38\times F \text{ [\%]}+0.21\times P \text{ [\%]})/3.28)\times M \text{ [kg/day]} \qquad \text{—equation 2—}$$

wherein:
    "M" means the total amount of milk of a dairy cow per one day as determined in a);
    "F" means the weight percentage amount of fat contained in the milk of the dairy cow per one day as determined in a); and
    "P" means the weight percentage amount of protein contained in the milk of a dairy cow per one day as determined in a).

6. The method according to claim 3, wherein the weight percentage amount of saturated fatty acids (SFAs) of the total milk fat according to c) is at least the sum of the weight percentage amounts of butanoic acid (C4:0), hexanoic acid (C6:0), octanoic acid (C8:0), capric acid (C10:0), lauric acid (C12:0), iso-lauric acid (C12:0-iso), anteiso-lauric acid (C12:0-anteiso), tridecanoic acid (C13:0), myristic acid (C14:0), iso-myristic acid (C14:0-iso), anteiso-myristic acid (C14:0-anteiso), pentadecanoic acid (C15:0), iso-pentadecanoic acid (C15:0-iso), palmitic acid (C16:0), iso-palmitic acid (C16:0-iso), anteiso-palmitic acid (C16:0-anteiso), heptadecanoic acid (C17:0), iso-heptadecanoic acid (C17:0-iso), anteiso-heptadecanoic acid (C17:0-anteiso), stearic acid (C18:0), nonadecanoic acid (C19:0), eicosanoic acid (C20:0) and docosanoic acid (C22:0) of the total milk fat.

* * * * *